United States Patent
Badenes et al.

(10) Patent No.: US 9,814,420 B2
(45) Date of Patent: Nov. 14, 2017

(54) BURNOUT SYMPTOMS DETECTION AND PREDICTION

(71) Applicant: INTERNATIONAL BUSINESS MACHINES CORPORATION, Armonk, NY (US)

(72) Inventors: Hernan Badenes, Neuquen (AR); Marco P. Crasso, Buenos Aires (AR); Patricio M. Reyna Almandos, Buenos Aires (AR)

(73) Assignee: International Business Machines Corporation, Armonk, NY (US)

( * ) Notice: Subject to any disclaimer, the term of this patent is extended or adjusted under 35 U.S.C. 154(b) by 21 days.

(21) Appl. No.: 15/064,751

(22) Filed: Mar. 9, 2016

(65) Prior Publication Data

US 2017/0258384 A1    Sep. 14, 2017

(51) Int. Cl.
*G08B 23/00* (2006.01)
*A61B 5/16* (2006.01)
(Continued)

(52) U.S. Cl.
CPC .............. *A61B 5/165* (2013.01); *G08B 21/02* (2013.01); *H04L 51/02* (2013.01); *H04L 67/22* (2013.01)

(58) Field of Classification Search
CPC ......... A61B 5/165; G08B 21/02; H04L 51/02; H04L 67/22
(Continued)

(56) References Cited

U.S. PATENT DOCUMENTS

| 2013/0013208 A1* | 1/2013 | Ohnemus | ............ G06F 19/3431 702/3 |
| 2014/0205986 A1* | 7/2014 | Pillay | ...................... G09B 7/02 434/335 |

(Continued)

FOREIGN PATENT DOCUMENTS

| CN | 103747722 A | 4/2014 |
| WO | 2008055078 A2 | 5/2008 |
| WO | 2014145228 A1 | 9/2014 |

OTHER PUBLICATIONS

American Management Association, "How to Prevent Burnout and Improve Productivity," AMA Training Articles, Feb. 15, 2006, p. 1-2, http://www.amanet.org/training/articles/printversion/How-to-Prevent-Burnout-and-Improve-Productivity.aspx, Accessed on Mar. 8, 2016.

(Continued)

*Primary Examiner* — Naomi Small
(74) *Attorney, Agent, or Firm* — Reza Sarbakhsh

(57) ABSTRACT

A method for detecting and presenting burnout symptoms associated with users is provided. The method may include receiving a plurality of predictor rules for monitoring and detecting a plurality of burnout indicators. The method may further include monitoring and receiving the plurality of burnout indicators. Additionally, the method may include storing the monitored and received plurality of burnout indicators. The method may also include detecting a plurality of burnout events associated with the stored monitored and received plurality of burnout indicators. The method may further include determining the plurality of burnout symptoms based on the detected plurality of burnout events. The method may also include determining at least one aggregate score based on the determined plurality of burnout symptoms. The method may further include presenting at least one alert and at least one recommendation based on the (Continued)

determined plurality of burnout symptoms and the determined at least one aggregate score.

20 Claims, 6 Drawing Sheets

(51) Int. Cl.
*G08B 21/02* (2006.01)
*H04L 29/08* (2006.01)
*H04L 12/58* (2006.01)

(58) Field of Classification Search
USPC ........................................... 340/573.1
See application file for complete search history.

(56) References Cited

U.S. PATENT DOCUMENTS

| | | | |
|---|---|---|---|
| 2015/0024358 A1* | 1/2015 | Kamiya | G06F 19/3431 434/236 |
| 2015/0265212 A1* | 9/2015 | Bruekers | A61B 5/6892 600/301 |
| 2016/0151603 A1* | 6/2016 | Shouldice | H04R 3/00 600/28 |

OTHER PUBLICATIONS

Dewa et al., "How Does Burnout Affect Physician Productivity? A Systematic Literature Review," BMC Health Services Research, 2014, p. 1-10, BioMed Central Ltd.

Dornostup, "Pervasive Computing for Early Burnout Detection," Eindhoven University of Technology Master Thesis, 2014, p. 1-49.

Hoeven et al., "Organizational Communication and Burnout Symptoms," International Communication Association Conference, Jun. 19-23, 2006, p. 1-30, Dresden, Germany.

Hudek-Knežević et al., "Personality, Organizational Stress, and Attitudes Toward Work as Prospective Predictors of Professional Burnout in Hospital Nurses," Croatian Medical Journal, Aug. 2011, p. 538-549, vol. 52, Issue 4.

IBM, "Personality Insights," IBM Watson Developer Cloud, p. 1-5, http://www.ibm.com/smarterplanet/us/en/ibmwatson/developercloud/personality-insights.html, Accessed on Feb. 3, 2016.

IBM, "Tone Analyzer," IBM Watson Developer Cloud, p. 1-3, https://www.ibm.com/smarterplanet/us/en/ibmwatson/developercloud/tone-analyzer.html, Accessed on Feb. 3, 2016.

Ji et al., "A Probabilistic Framework for Modeling and Real-Time Monitoring Human Fatigue," IEEE Transactions on Systems, Man, and Cybernetics—Part A: Systems and Humans, Sep. 2006, p. 862-875, vol. 36, No. 5.

Kesler, "Burnout: A Multimodal Approach to Assessment and Resolution," Elementary School Guidance & Counseling, Apr. 1990, p. 303-311, vol. 24, No. 4, Special Issue on Multimodal Theory, Research, and Practice, American School Counselor Association.

Kirk-Brown et al., "Predicting Burnout and Job Satisfaction in Workplace Counselors: The Influence of Role Stressors, Job Challenge, and Organizational Knowledge," Journal of Employment Counseling, Mar. 2004, p. 29-37, vol. 41.

Linzer et al., "Predicting and Preventing Physician Burnout: Results from the United States and the Netherlands," The American Journal of Medicine, Aug. 1, 2001, p. 170-175, vol. 111, Association of Professors of Medicine (ARM), Excerpta Medica, Inc.

Magnano et al., "Relationships between Personality and Burn-Out: An Empirical Study with Helping Professions' Workers," International Journal of Humanities and Social Science Research, 2015, p. 10-19, vol. 1, Lifescience Global.

Maslach et al., "Early Predictors of Job Burnout and Engagement," Journal of Applied Psychology, 2008, p. 498-512, vol. 93, No. 3, American Psychological Association.

Mell et al., "The NIST Definition of Cloud Computing," National Institute of Standards and Technology, Sep. 2011, p. 1-3, Special Publication 800-145.

\* cited by examiner

BURNOUT SYMPTOMS DETECTION AND PREDICTION

BACKGROUND

The present invention relates generally to the field of computing, and more specifically, to data collection and analysis.

Generally, burnout is a state of emotional, mental, and physical exhaustion caused by excessive and prolonged stress that may occur to individuals when feeling overwhelmed and unable to meet constant demands. Typically, causes of burnout may be based on work-related stress and activity, individual lifestyle, and personality traits. Specifically, factors that contribute to burnout may include overly demanding job expectations, overwhelming responsibilities, lack of sleep, lack of a social life, and pessimism. Furthermore, the factors that contribute to burnout may lead to burnout symptoms such as fatigue, head and muscle aches, emotional detachment, withdrawal, and changes in eating and sleeping patterns. Typical burnout detection techniques focus on the physical conditions associated with burnouts, and may include measuring changes in heartbeat and physical fatigue.

SUMMARY

A method for detecting and presenting a plurality of burnout symptoms associated with at least one user is provided. The method may include receiving a plurality of predictor rules for monitoring and detecting a plurality of burnout indicators. The method may further include monitoring and receiving the plurality of burnout indicators. Additionally, the method may include storing the monitored and received plurality of burnout indicators. The method may also include detecting a plurality of burnout events associated with the stored monitored and received plurality of burnout indicators. The method may further include determining the plurality of burnout symptoms based on the detected plurality of burnout events. The method may also include determining at least one aggregate score based on the determined plurality of burnout symptoms. The method may further include presenting at least one alert and at least one recommendation based on the determined plurality of burnout symptoms and the determined at least one aggregate score.

A computer system for detecting and presenting a plurality of burnout symptoms associated with at least one user is provided. The computer system may include one or more processors, one or more computer-readable memories, one or more computer-readable tangible storage devices, and program instructions stored on at least one of the one or more storage devices for execution by at least one of the one or more processors via at least one of the one or more memories, whereby the computer system is capable of performing a method. The method may include receiving a plurality of predictor rules for monitoring and detecting a plurality of burnout indicators. The method may further include monitoring and receiving the plurality of burnout indicators. Additionally, the method may include storing the monitored and received plurality of burnout indicators. The method may also include detecting a plurality of burnout events associated with the stored monitored and received plurality of burnout indicators. The method may further include determining the plurality of burnout symptoms based on the detected plurality of burnout events. The method may also include determining at least one aggregate score based on the determined plurality of burnout symptoms. The method may further include presenting at least one alert and at least one recommendation based on the determined plurality of burnout symptoms and the determined at least one aggregate score.

A computer program product for detecting and presenting a plurality of burnout symptoms associated with at least one user is provided. The computer program product may include one or more computer-readable storage devices and program instructions stored on at least one of the one or more tangible storage devices, the program instructions executable by a processor. The computer program product may include program instructions to receive a plurality of predictor rules for monitoring and detecting a plurality of burnout indicators. The computer program product may further include program instructions to monitor and receive the plurality of burnout indicators. Additionally, the computer program product may also include program instructions to store the monitored and received plurality of burnout indicators. The computer program product may further include program instructions to detect a plurality of burnout events associated with the stored monitored and received plurality of burnout indicators. The computer program product may also include program instructions to determine the plurality of burnout symptoms based on the detected plurality of burnout events. The computer program product may further include program instructions to determine at least one aggregate score based on the determined plurality of burnout symptoms. The computer program product may also include program instructions to present at least one alert and at least one recommendation based on the determined plurality of burnout symptoms and the determined at least one aggregate score.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
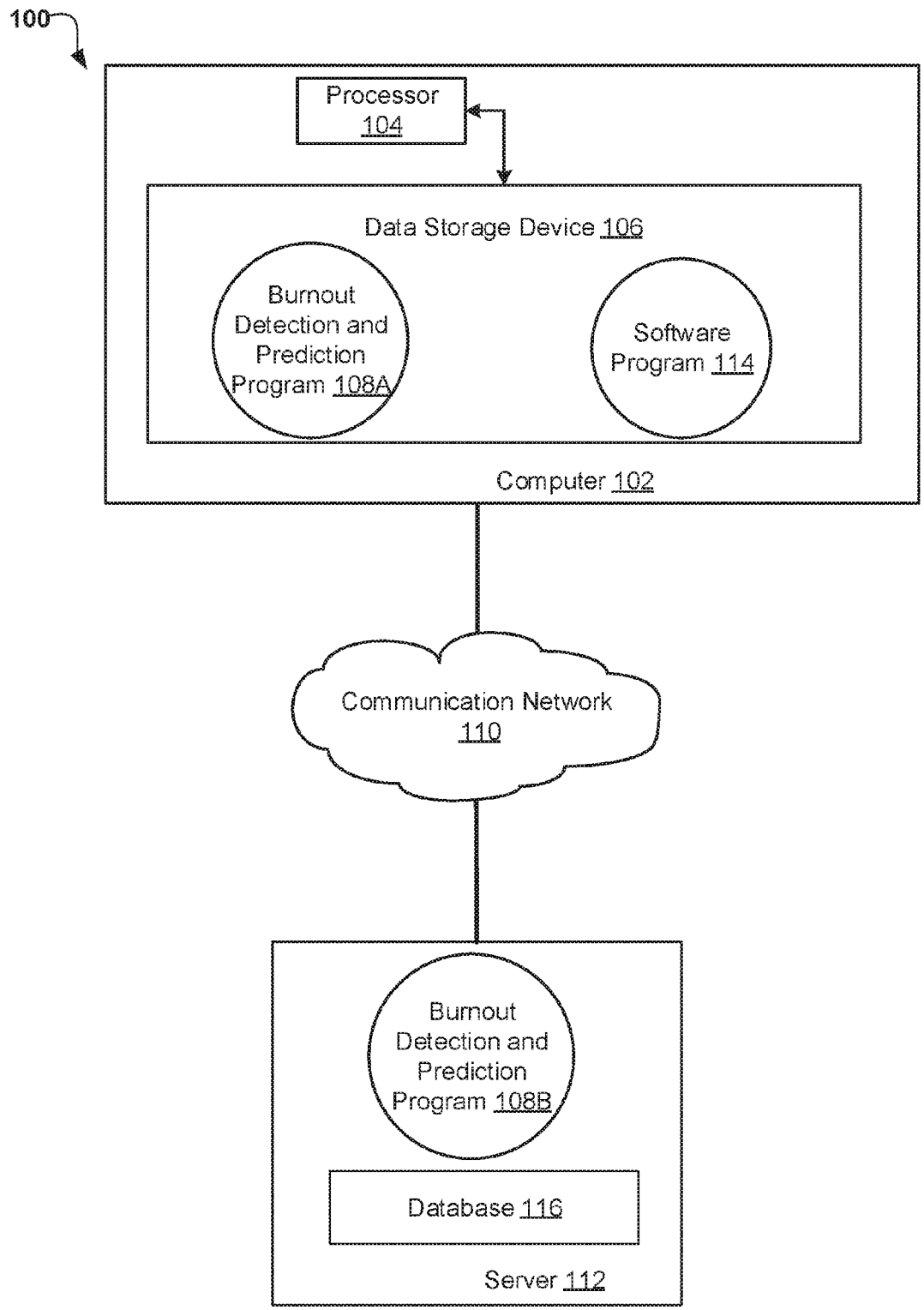
FIG. 1 illustrates a networked computer environment according to one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Embodiments of the present invention relate generally to the field of computing, and more particularly, to data collection and analysis. The following described exemplary embodiments provide a system, method and program product for detecting burnout symptoms. Therefore, the present embodiment has the capacity to improve the technical field associated with burnout symptoms detection by monitoring and receiving sets of behavior indicators. Specifically, the present embodiment may use detectors to monitor and receive behavior indicators, and may use predictors to detect events associated with the behavior indicators to determine whether burnout symptoms are present.

As previously described with respect to burnout symptoms, burnouts may be based on work-related stress and activity, lifestyle, and personality traits. Furthermore, the factors that contribute to burnouts may lead to burnout symptoms such as fatigue, head and muscle aches, emotional detachment, withdrawal, and changes in eating and sleeping patterns. However, as previously described, current burnout detection techniques are typically limited to the physical conditions associated with burnouts and may be obtrusive, such as measuring changes in heartbeat and physical fatigue. Therefore, the current burnout detection techniques may be limited in detecting burnouts, and predicting when burnouts occur, based on the limited information derived from measuring physical conditions as opposed to detecting and measuring additional information such as lifestyle and personality traits. As such, it may be advantageous, among other things, to provide a system, method and program product for detecting burnout symptoms by monitoring user psychological, sociological and working environment conditions. Specifically, the present embodiment may use detectors to detect and measure working activities, social activities, and personality traits associated with users, and may use predictors to measure changes in the detected and measured working activities, social activities, and personality traits, to determine whether burnout symptoms are present.

According to at least one implementation of the present embodiment, predictor rules for monitoring and receiving burnout indicators may be received. Then, burnout indicators may be monitored and received. Next, the monitored and received burnout indictors may be stored. Then, burnout events associated with the stored monitored and received burnout indicators may be detected based on the received predictor rules. Thereafter, based on the detected burnout events, burnout symptoms may be determined. Next, aggregate scores based on the determined burnout symptoms may be determined. Then, alerts may be presented based on the determined burnout symptoms and the aggregate scores.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for determining and providing aggregate functions associated with database tables.

According to at least one implementation, predictor rules for monitoring and receiving burnout indicators may be received. Then, burnout indicators may be monitored and received. Next, the monitored and received burnout indictors may be stored. Then, burnout events associated with the stored monitored and received burnout indicators may be detected based on the received predictor rules. Thereafter, based on the detected burnout events, burnout symptoms may be determined. Next, aggregate scores based on the determined burnout symptoms may be determined. Then, alerts may be presented based on the determined burnout symptoms and the aggregate scores.

Referring now to FIG. 1, an exemplary networked computer environment 100 in accordance with one embodiment is depicted. The networked computer environment 100 may include a computer 102 with a processor 104 and a data storage device 106 that is enabled to run a burnout detection and prediction program 108A and a software program 114. The software program 114 may be an application program such as an internet browser and an email program. The burnout detection and prediction program 108A may communicate with the software program 114. The networked computer environment 100 may also include a server 112 that is enabled to run a burnout detection and prediction program 108B and a communication network 110. The networked computer environment 100 may include a plurality of computers 102 and servers 112, only one of which is shown for illustrative brevity.

According to at least one implementation, the present embodiment may also include a database 116, which may be running on server 112. The communication network 110 may include various types of communication networks, such as a wide area network (WAN), local area network (LAN), a telecommunication network, a wireless network, a public switched network and/or a satellite network. It may be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with server computer 112 via the communications network 110. The communications network 110 may include connections, such as wire, wireless communication links, or fiber optic cables. As will be discussed with reference to FIG. 4, server computer 112 may include internal components 800a and external components 900a, respectively, and client computer 102 may include internal components 800b and external components 900b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing device capable of running a program and accessing a network. According to various implementations of the present embodiment, the burnout detection and prediction program 108A, 108B may interact with a database 116 that may be embedded in various storage devices, such as, but not limited to a mobile device 102, a networked server 112, or a cloud storage service.

According to the present embodiment, a program, such as a burnout detection and prediction program 108A and 108B, may run on the client computer 102 or on the server computer 112 via a communications network 110. The burnout detection and prediction program 108A, 108B may detect burnout symptoms. Specifically, a user using a computer, such as computer 102, may run a burnout detection and prediction program 108A, 108B that interacts with a software program 114, such as an email program, to monitor and receive burnout indicators associated with users, detect changes to the burnout indicators to determine whether burnout symptoms are present, and provide alerts and recommendations based on the burnout symptoms.

Figure 2:
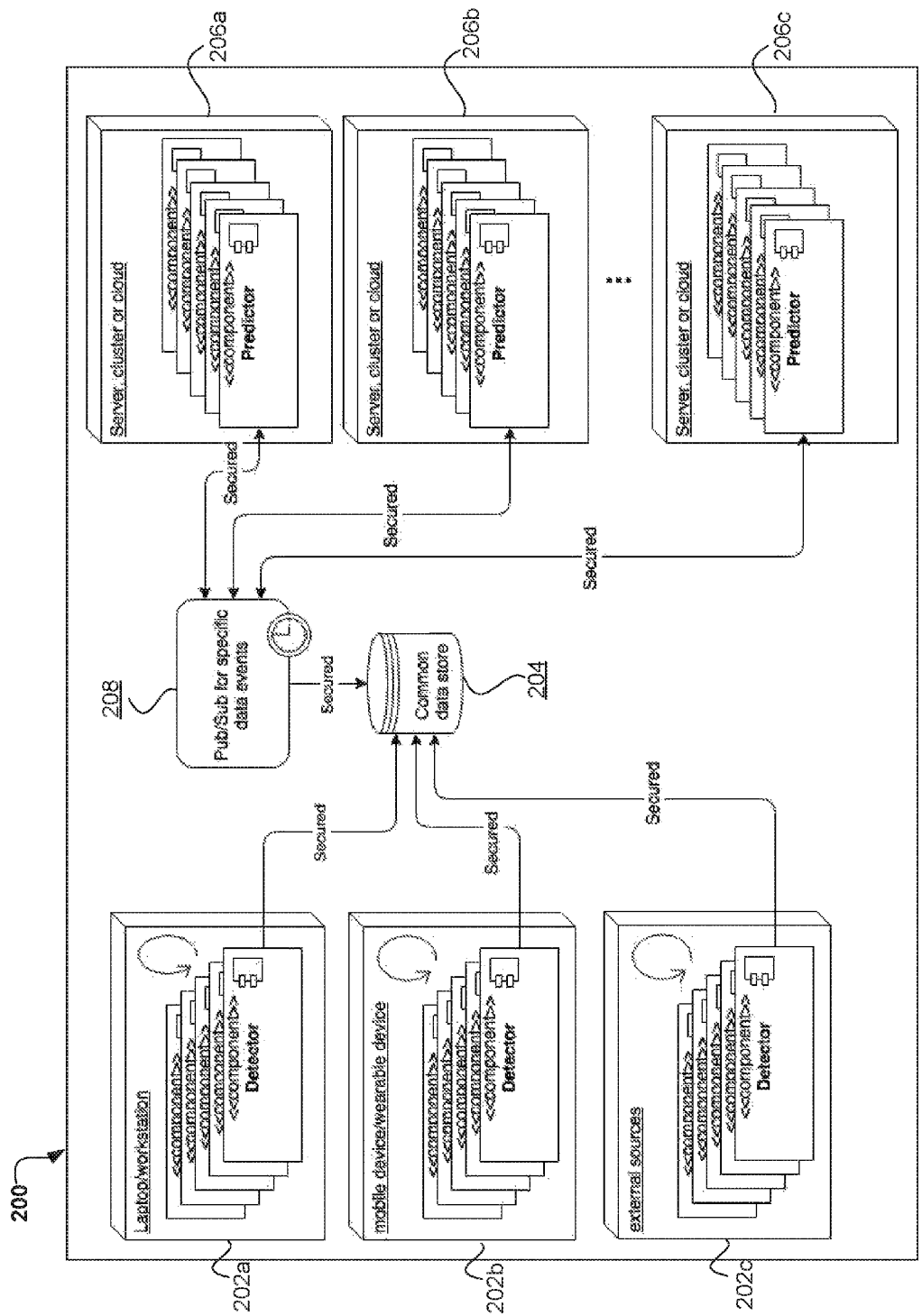
FIG. 2 is a block diagram illustrating the system architecture of burnout detection and prediction program according to one embodiment.

Referring now to FIG. 2, a block diagram 200 illustrating the system architecture of program for detecting and presenting burnout symptoms in accordance with one embodiment is depicted. As previously described, the burnout detection and prediction program 108A, 108B (FIG. 1) may detect burnout symptoms by monitoring and receiving burnout indicators. Specifically, the burnout detection and prediction program 108A, 108B (FIG. 1) may monitor and receive burnout indicators by using detectors 202a, 202b, and 202c such as laptops/workstations 202a, mobile devices/wearable devices 202b, and external sources 202c, such as email servers and cloud repositories. Furthermore, the burnout detection and prediction program 108A, 108B (FIG. 1) may monitor and receive burnout indicators, such as user psychological and personality traits, levels of activity, communication tone, work-life balance, and fitness and sleep activity.

For example, the burnout detection and prediction program 108A, 108B (FIG. 1) may use the detectors 202a, 202b, and 202c to monitor and receive user psychological and personality traits by using IBM Watson™ Personality Insights (IBM Watson and all Watson-based trademarks and logos are trademarks of International Business Machines Corporation and/or its affiliates) to analyze user speeches and written text in communications. Furthermore, for example, the burnout detection and prediction program 108A, 108B (FIG. 1) may use the detectors 202a, 202b, and 202c to monitor and receive user tones and attitudes associated with communications by using IBM Watson™ Tone Analyzer to analyze written text, such as emails and documents. Also, for example, the burnout detection and prediction program 108A, 108B (FIG. 1) may use the detectors 202a, 202b, and 202c to monitor and receive user levels of activity by analyzing user email activity and calendar schedule. Additionally, for example, the burnout detection and prediction program 108A, 108B (FIG. 1) may use the detectors 202a, 202b, and 202c to monitor and receive user work-life balance by analyzing user calendars to determine vacation periods and out-of-office calendar entries. Also, for example, the burnout detection and prediction program 108A, 108B (FIG. 1) may use the detectors 202a, 202b, and 202c, such as wearable devices, to monitor and receive the user fitness and sleep patterns. Furthermore, the burnout detection and prediction program 108A, 108B (FIG. 1) may include a data store 204 to store the monitored and received burnout indicators and the information associated with the burnout indicators.

Thereafter, the burnout detection and prediction program 108A, 108B (FIG. 1) may include predictors 206a, 206b, and 206c, such as servers and cloud servers, that may further include predictor rules to determine whether burnout symptoms are present based on the monitored and received burnout indicators that are stored on the data store 204. For example, for a burnout symptom such as pessimism, the burnout detection and prediction program 108A, 108B (FIG. 1) may include a detector 202a to analyze written text for negative sentences and to store the analyzed written text on data store 204. Furthermore, the burnout detection and prediction program 108A, 108B (FIG. 1) may include messaging services, such as a publish-subscribe (pub/sub) messaging service 208, to enable the detectors 202a, 202b, and 202c to communicate with the predictors 206a, 206b, and 206c. Therefore, the burnout detection and prediction program 108A, 108B (FIG. 1) may use a predictor 206a that may further include a predictor rule that detects whether a threshold value of 70% of a user's written text includes negative sentences. As such, based on the predictor rule associated with the predictor 206a, the burnout detection and prediction program 108A, 108B (FIG. 1) may present an alert when it is determined that 70% of the stored written text includes negative sentences.

Figure 3:
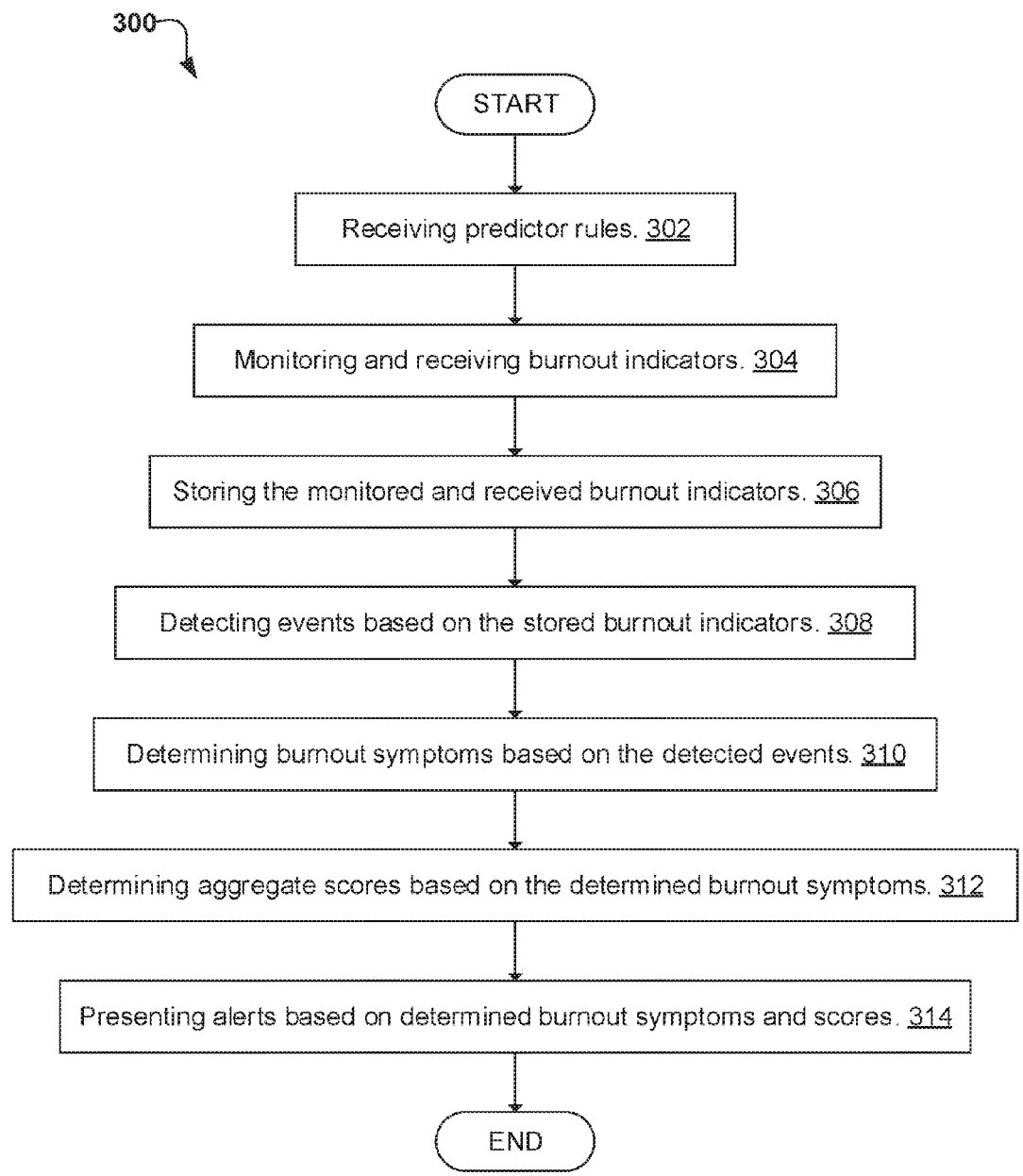
FIG. 3 is an operational flowchart illustrating the steps carried out by a program for detecting and presenting burnout symptoms according to one embodiment.

Referring now to FIG. 3, an operational flowchart 300 illustrating the steps carried out by a program for detecting burnout symptoms in accordance with one embodiment is depicted. At 302, the burnout detection and prediction program 108A, 108B (FIG. 1) may receive predictor rules. Specifically, and as previously described in FIG. 2, the burnout detection and prediction program 108A, 108B (FIG. 1) may include predictors 206a, 206b, and 206c (FIG. 2) that may further include predictor rules to detect whether burnout symptoms are present based on monitored and received burnout indicators that are stored on the data store 204 (FIG. 2). For example, for a burnout symptom such as lack of sleep, the burnout detection and prediction program 108A, 108B (FIG. 1) may include a predictor 206b (FIG. 2) that may further include a predictor rule that detects when a user gets less than 42 hours of sleep per week.

Next, at 304, the burnout detection and prediction program 108A, 108B (FIG. 1) may monitor and receive the burnout indicators. As previously described in FIG. 2, the burnout detection and prediction program 108A, 108B (FIG. 1) may use detectors 202a, 202b, and 202c (FIG. 2), such as laptops/workstations 202a (FIG. 2), mobile devices/wearable devices 202b (FIG. 2), and external sources 202c (FIG. 2), such as email servers and cloud repositories, to monitor burnout indicators, such as user psychological and personality traits, levels of activity, communication tone, work-life balance, and fitness and sleep activity. For example, the burnout detection and prediction program 108A, 108B (FIG. 1) may use the detectors 202a, 202b, and 202c (FIG. 2) to monitor and receive user psychological and personality traits by using IBM Watson™ Personality Insights to monitor, receive, and analyze user speeches and written text in communications.

Thereafter, at step 306, the burnout detection and prediction program 108A, 108B (FIG. 1) may store the monitored and received burnout indicators. Specifically, and as previously described in FIG. 2, the burnout detection and prediction program 108A, 108B (FIG. 1) may store the monitored and received burnout indicators on the data store 204 (FIG. 2). For example, the burnout detection and prediction program 108A, 108B (FIG. 1) may monitor and receive burnout indicators based on received user speeches and written text, received user email activity and calendar entries, and received user fitness and sleep patterns. Next, the burnout detection and prediction program 108A, 108B (FIG. 1) may store the received user speeches and written text, the received user email activity and calendar entries, and the received user fitness and sleep patterns on the data store 204 (FIG. 2).

Then, at 308, the burnout detection and prediction program 108A, 108B (FIG. 1) may detect burnout events associated with the stored monitored and received burnout indicators. Specifically, the burnout detection and prediction program 108A, 108B (FIG. 1) may use predictors 206a, 206b, and 206c (FIG. 2) to detect burnout events associated with the stored monitored and received burnout indicators based on the predictor rules. As previously described at step 302, the burnout detection and prediction program 108A, 108B (FIG. 1) may include predictors 206a, 206b, and 206c (FIG. 2) that may further include predictor rules to determine whether burnout symptoms are present based on the monitored and received burnout indicators that are stored on the data store 204 (FIG. 2). For example, for a burnout symptom such as pessimism, the burnout detection and prediction program 108A, 108B (FIG. 1) may include a detector 202a (FIG. 2) to monitor and receive written text, and to store the written text on the data store 204 (FIG. 2). Additionally, the burnout detection and prediction program 108A, 108B (FIG. 1) may include a predictor 206a (FIG. 2) that may further include a predictor rule to detect when a threshold value of 70% of a user's written text includes negative sentences. Therefore, based on the predictor rule, the burnout detection and prediction program 108A, 108B (FIG. 1) may use the predictor 206a (FIG. 2) to detect burnout events such as whether 70% of the stored written text includes negative sentences.

Next, at 310, the burnout detection and prediction program 108A, 108B (FIG. 1) may determine burnout symptoms based on the detected burnout events. As previously described at step 308, the burnout detection and prediction program 108A, 108B (FIG. 1) may use predictors 206a, 206b, and 206c (FIG. 2) to detect burnout events associated with the stored monitored and received burnout indicators based on the predictor rules. For example, the burnout detection and prediction program 108A, 108B (FIG. 1) may include a predictor 206a (FIG. 2) that may include a predictor rule to detect a burnout event such as whether a threshold value of 70% of a user's written text includes negative sentences, and may include a predictor 206b (FIG. 2) to detect a burnout event such as when a user gets less than 42 hours of sleep per week. As such, based on the predictors 206a, 206b (FIG. 2) and the detected burnout events, the burnout detection and prediction program 108A, 108B (FIG. 1) may determine that the burnout symptoms pessimism and lack of sleep may be present.

Then, at 312, the burnout detection and prediction program 108A, 108B (FIG. 1) may determine aggregate scores based on the determined burnout symptoms. Specifically, the burnout detection and prediction program 108A, 108B (FIG. 1) may determine aggregate scores that represent the probability for burnouts. For example, based on the predictors 206a, 206b, and 206c (FIG. 2) and the detected burnout events, the burnout detection and prediction program 108A, 108B (FIG. 1) may determine burnout symptoms such as lack of free time, neuroticism, lack of sleep, and aggressive tones of communication may be present. Therefore, the burnout detection and prediction program 108A, 108B (FIG. 1) may determine there is a 65% probability for a burnout.

Next, at 314, the burnout detection and prediction program 108A, 108B (FIG. 1) may present alerts and recommendations based on the determined burnout symptoms and the determined aggregate scores. As previously described at step 310, the burnout detection and prediction program 108A, 108B (FIG. 1) may determine burnout symptoms based on burnout events detected by the predictors 206a, 206b, and 206c (FIG. 2). Furthermore, at step 312, the burnout detection and prediction program 108A, 108B (FIG. 1) may determine aggregate scores based on the determined burnout symptoms. As such, the burnout detection and prediction program 108A, 108B (FIG. 1) may present users with alerts that may include the determined burnout symptoms and the determined aggregate scores, as well as recommendations to reduce the burnout symptoms. For example, the burnout detection and prediction program 108A, 108B (FIG. 1) may recommend not extending work activity beyond certain hours and getting more sleep. Furthermore, the burnout detection and prediction program 108A, 108B (FIG. 1) may present the alerts using messaging, instant messaging, phone and email communications.

It may be appreciated that FIGS. 2 and 3 provide only illustrations of one implementation and do not imply any limitations with regard to how different embodiments may be implemented. Many modifications to the depicted environments may be made based on design and implementation requirements.

Figure 4:
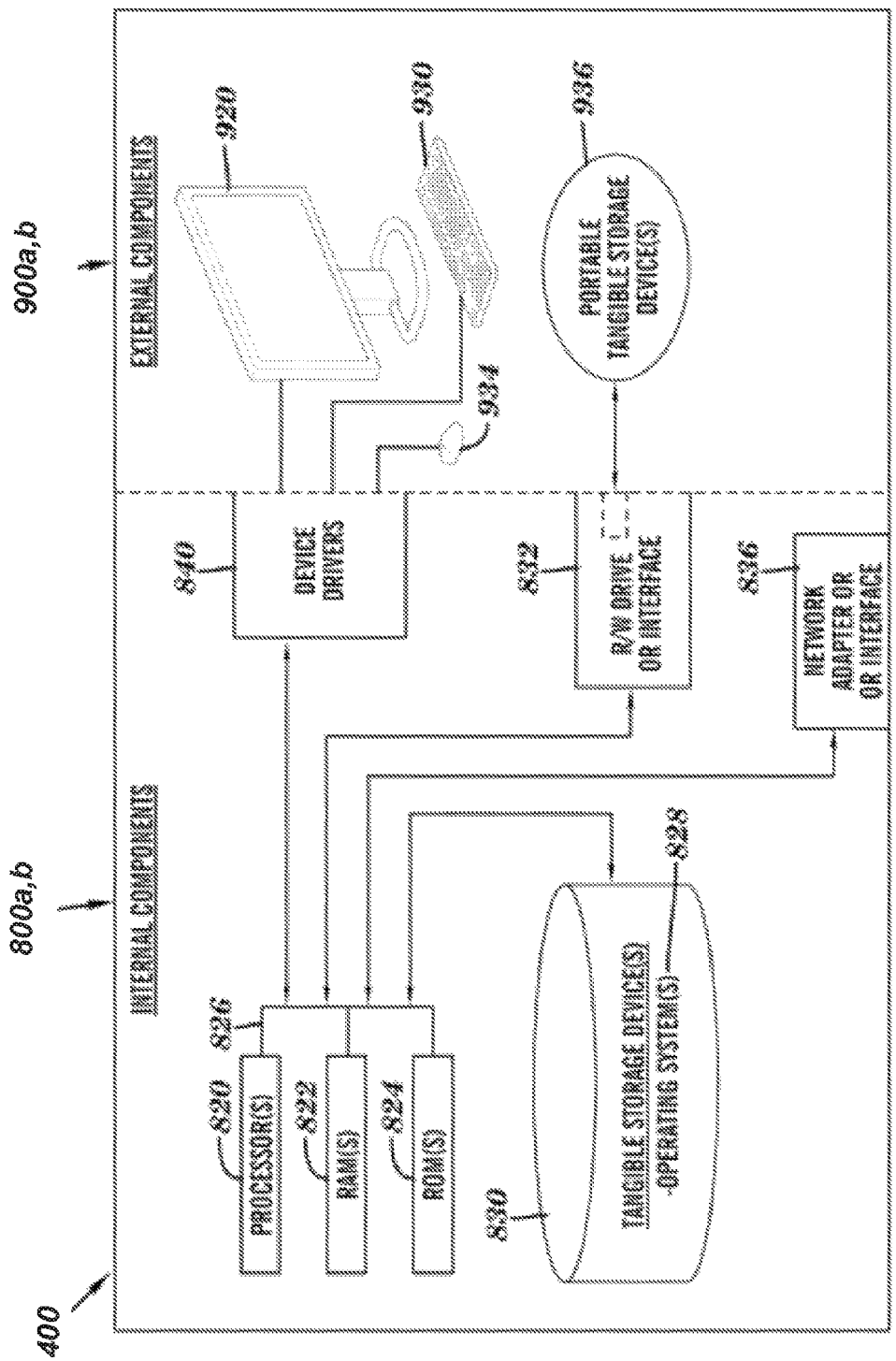
FIG. 4 is a block diagram of the system architecture of a program for detecting and presenting burnout symptoms according to one embodiment.

FIG. 4 is a block diagram 400 of internal and external components of computers depicted in FIG. 1 in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

Data processing system 800, 900 is representative of any electronic device capable of executing machine-readable program instructions. Data processing system 800, 900 may be representative of a smart phone, a computer system, PDA, or other electronic devices. Examples of computing systems, environments, and/or configurations that may be represented by data processing system 800, 900 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 (FIG. 1), and network server 112 (FIG. 1) include respective sets of internal components 800 *a, b* and external components 900 *a, b* illustrated in FIG. 4. Each of the sets of internal components 800 *a, b* includes one or more processors 820, one or more computer-readable RAMs 822, and one or more computer-readable ROMs 824 on one or more buses 826, and one or more operating systems 828 and one or more computer-readable tangible storage devices 830. The one or more operating systems 828, the software program 114 (FIG. 1), the burnout detection and prediction program 108A (FIG. 1) in client computer 102 (FIG. 1), and the burnout detection and prediction program 108B (FIG. 1) in network server computer 112 (FIG. 1) are stored on one or more of the respective computer-readable tangible storage devices 830 for execution by one or more of the respective processors 820 via one or more of the respective RAMs 822 (which typically include cache memory). In the embodiment illustrated in FIG. 4, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800 *a, b*, also includes a R/W drive or interface 832 to read from and write to one or more portable computer-readable tangible storage devices 936 such as a CD-ROM, DVD, memory stick, magnetic tape, magnetic disk, optical disk or semiconductor storage device. A software program, such as a burnout detection and prediction program 108A and 108B (FIG. 1), can be stored on one or more of the respective portable computer-readable tangible storage devices 936, read via the respective R/W drive or interface 832 and loaded into the respective hard drive 830.

Each set of internal components 800 *a, b* also includes network adapters or interfaces 836 such as a TCP/IP adapter cards, wireless Wi-Fi interface cards, or 3G or 4G wireless interface cards or other wired or wireless communication links. The burnout detection and prediction program 108A (FIG. 1) and software program 114 (FIG. 1) in client computer 102 (FIG. 1), and the burnout detection and prediction program 108B (FIG. 1) in network server 112 (FIG. 1) can be downloaded to client computer 102 (FIG. 1) from an external computer via a network (for example, the Internet, a local area network or other, wide area network) and respective network adapters or interfaces 836. From the network adapters or interfaces 836, the burnout detection and prediction program 108A (FIG. 1) and software program 114 (FIG. 1) in client computer 102 (FIG. 1) and the burnout detection and prediction program 108B (FIG. 1) in network server computer 112 (FIG. 1) are loaded into the respective hard drive 830. The network may comprise copper wires, optical fibers, wireless transmission, routers, firewalls, switches, gateway computers and/or edge servers.

Each of the sets of external components 900 a, b can include a computer display monitor 920, a keyboard 930, and a computer mouse 934. External components 900 a, b can also include touch screens, virtual keyboards, touch pads, pointing devices, and other human interface devices. Each of the sets of internal components 800 a, b also includes device drivers 840 to interface to computer display monitor 920, keyboard 930, and computer mouse 934. The device drivers 840, R/W drive or interface 832, and network adapter or interface 836 comprise hardware and software (stored in storage device 830 and/or ROM 824).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
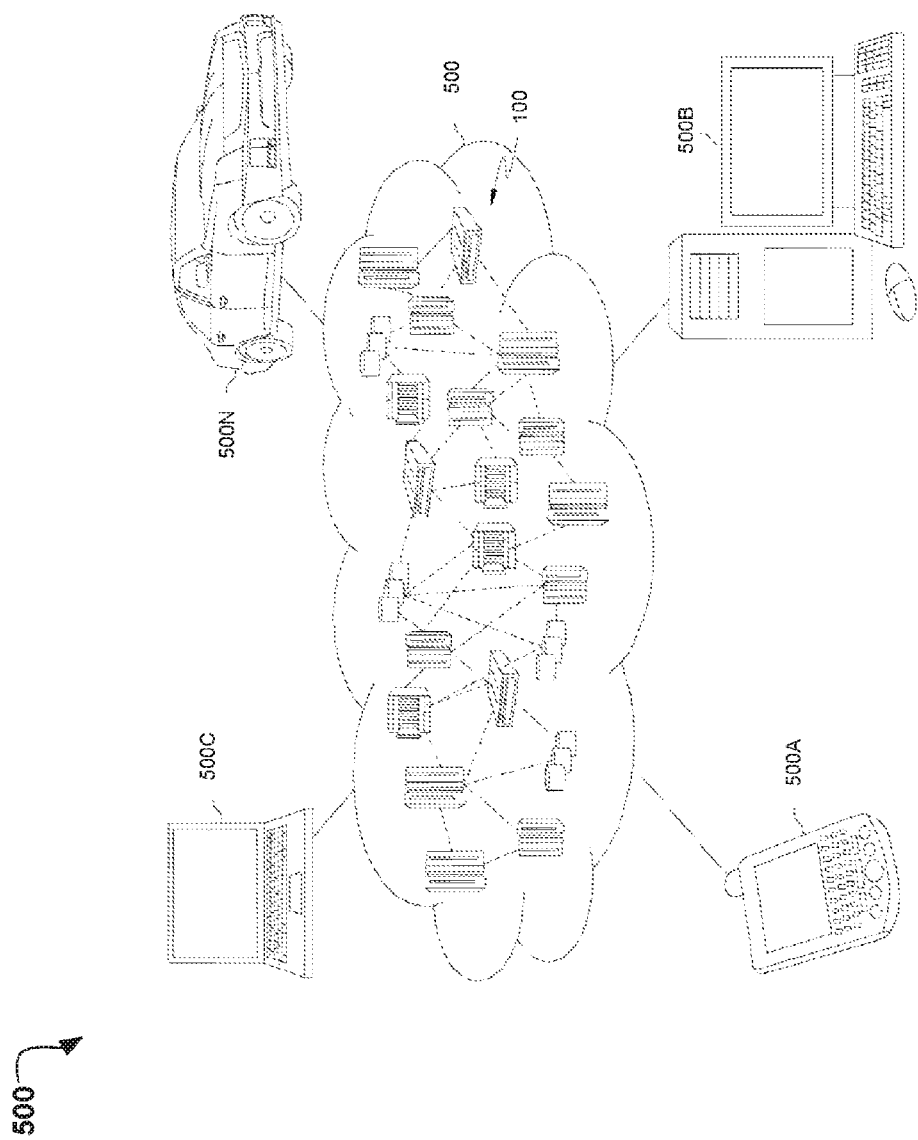
FIG. 5 is a block diagram of an illustrative cloud computing environment including the computer system depicted in FIG. 1, in accordance with an embodiment of the present disclosure.

Referring now to FIG. 5, illustrative cloud computing environment 500 is depicted. As shown, cloud computing environment 500 comprises one or more cloud computing nodes 100 with which local computing devices used by cloud consumers, such as, for example, personal digital assistant (PDA) or cellular telephone 500A, desktop computer 500B, laptop computer 500C, and/or automobile computer system 500N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 500 to offer infrastructure, platforms and/or software as services for which a cloud consumer does not need to maintain resources on a local computing device. It is understood that the types of computing devices 500A-N shown in FIG. 5 are intended to be illustrative only and that computing nodes 100 and cloud computing environment 500 can communicate with any type of computerized device over any type of network and/or network addressable connection (e.g., using a web browser).

Figure 6:
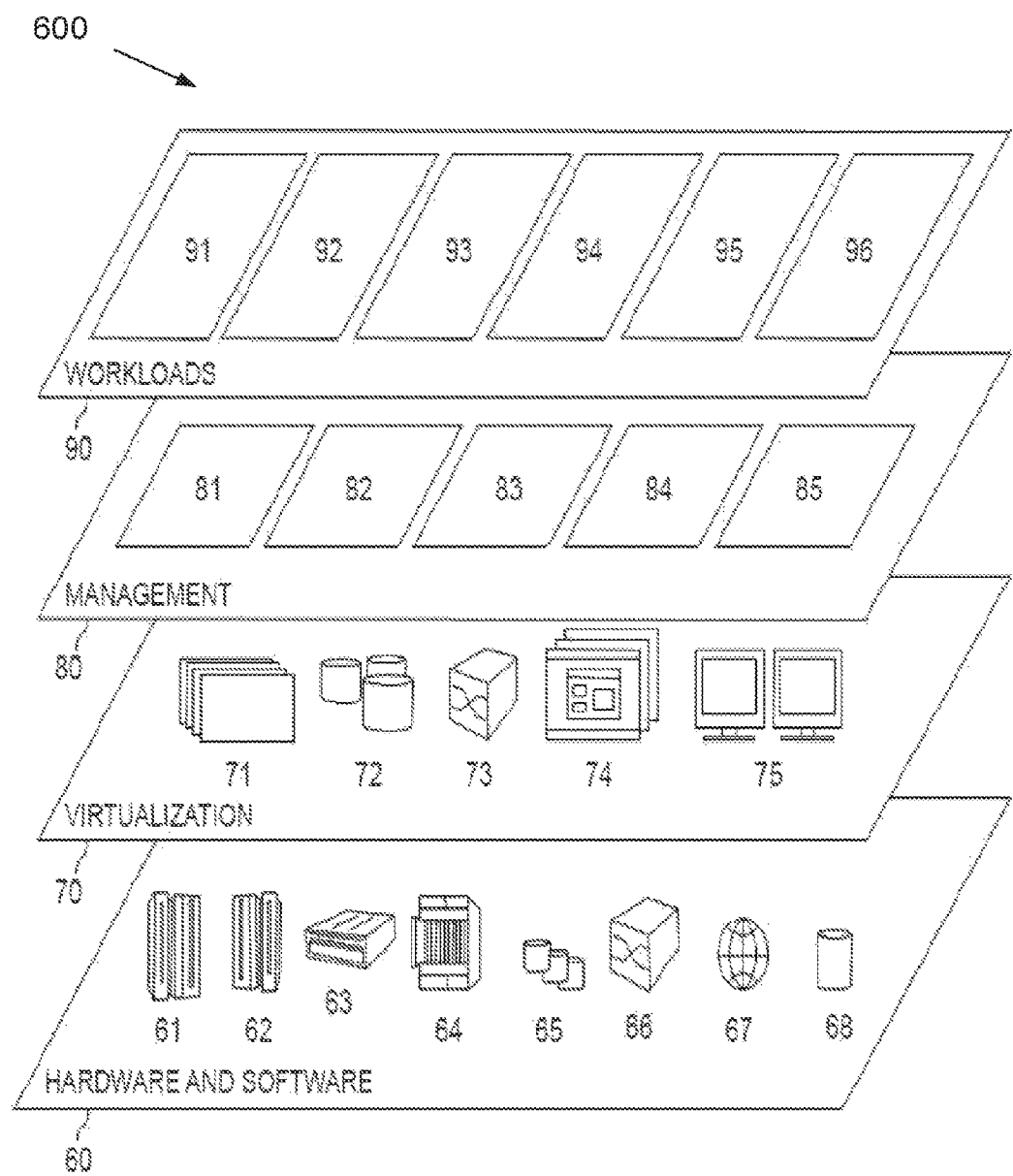
FIG. 6 is a block diagram of functional layers of the illustrative cloud computing environment of FIG. 5, in accordance with an embodiment of the present disclosure.

Referring now to FIG. 6, a set of functional abstraction layers 600 provided by cloud computing environment 500 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components.

Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and burnout detection and prediction 96. A burnout detection and prediction program 108A, 108B (FIG. 1) may be offered "as a service in the cloud" (i.e., Software as a Service (SaaS)) for applications running on mobile devices 102 (FIG. 1) and may detect burnout symptoms associated with users.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for detecting and presenting a plurality of burnout symptoms associated with at least one user, the method comprising:
   receiving a plurality of predictor rules for monitoring and detecting a plurality of burnout indicators;
   monitoring and receiving the plurality of burnout indicators;
   storing the monitored and received plurality of burnout indicators;
   detecting a plurality of burnout events associated with the stored monitored and received plurality of burnout indicators;
   determining the plurality of burnout symptoms based on the detected plurality of burnout events;
   determining at least one aggregate score based on the determined plurality of burnout symptoms; and
   presenting at least one alert and at least one recommendation based on the determined plurality of burnout symptoms and the determined at least one aggregate score.

2. The method of claim 1, wherein the plurality of burnout indicators are selected from a group comprising at least one of a plurality of written text, a plurality of emails, a plurality of calendar entries, and a plurality of wearable device data.

3. The method of claim 1, wherein monitoring and receiving the plurality of burnout indicators further comprises:
   using a plurality of detectors selected from a group comprising at least one of at least one workstation, at least one wearable device, at least one email server, and at least one cloud repository, to monitor and receive the plurality of burnout indicators.

4. The method of claim 1, wherein monitoring and receiving the plurality of burnout indicators further comprises:
   using IBM Watson™ Personality Insights and IBM Watson™ Tone Analyzer to analyze the plurality of burnout indicators.

5. The method of claim 1, wherein detecting the plurality of burnout events further comprises:
   using a plurality of predictors to detect the plurality of burnout events based on the received plurality of predictor rules.

6. The method of claim 5, wherein detecting a plurality of burnout events further comprises:
   using a publish-subscribe messaging service associated with the plurality of predictors to detect the plurality of burnout events.

7. The method of claim 1, wherein presenting the at least one alert and the at least one recommendation further comprises:
   using at least one of a messaging communication, a phone communication, and an email communication to present the at least one alert and the at least one recommendation.

8. A computer system for detecting and presenting a plurality of burnout symptoms associated with at least one user, comprising:
- one or more processors, one or more computer-readable memories, one or more computer-readable tangible storage devices, and program instructions stored on at least one of the one or more storage devices for execution by at least one of the one or more processors via at least one of the one or more memories, wherein the computer system is capable of performing a method comprising:
- receiving a plurality of predictor rules for monitoring and detecting a plurality of burnout indicators;
- monitoring and receiving the plurality of burnout indicators;
- storing the monitored and received plurality of burnout indicators;
- detecting a plurality of burnout events associated with the stored monitored and received plurality of burnout indicators;
- determining the plurality of burnout symptoms based on the detected plurality of burnout events;
- determining at least one aggregate score based on the determined plurality of burnout symptoms; and
- presenting at least one alert and at least one recommendation based on the determined plurality of burnout symptoms and the determined at least one aggregate score.

9. The computer system of claim 8, wherein the plurality of burnout indicators are selected from a group comprising at least one of a plurality of written text, a plurality of emails, a plurality of calendar entries, and a plurality of wearable device data.

10. The computer system of claim 8, wherein monitoring and receiving the plurality of burnout indicators further comprises:
- using a plurality of detectors selected from a group comprising at least one of at least one workstation, at least one wearable device, at least one email server, and at least one cloud repository, to monitor and receive the plurality of burnout indicators.

11. The computer system of claim 8, wherein monitoring and receiving the plurality of burnout indicators further comprises:
- using IBM Watson™ Personality Insights and IBM Watson™ Tone Analyzer to analyze the plurality of burnout indicators.

12. The computer system of claim 8, wherein detecting the plurality of burnout events further comprises:
- using a plurality of predictors to detect the plurality of burnout events based on the received plurality of predictor rules.

13. The computer system of claim 12, wherein detecting a plurality of burnout events further comprises:
- using a publish-subscribe messaging service associated with the plurality of predictors to detect the plurality of burnout events.

14. The computer system of claim 8, wherein presenting the at least one alert and the at least one recommendation further comprises:
- using at least one of a messaging communication, a phone communication, and an email communication to present the at least one alert and the at least one recommendation.

15. A computer program product for detecting and presenting a plurality of burnout symptoms associated with at least one user, comprising:
- one or more computer-readable storage devices and program instructions stored on at least one of the one or more tangible storage devices, the program instructions executable by a processor, the program instructions comprising:
- program instructions to receive a plurality of predictor rules for monitoring and detecting a plurality of burnout indicators;
- program instructions to monitor and receive the plurality of burnout indicators;
- program instructions to store the monitored and received plurality of burnout indicators;
- program instructions to detect a plurality of burnout events associated with the stored monitored and received plurality of burnout indicators;
- program instructions to determine the plurality of burnout symptoms based on the detected plurality of burnout events;
- program instructions to determine at least one aggregate score based on the determined plurality of burnout symptoms; and
- program instructions to present at least one alert and at least one recommendation based on the determined plurality of burnout symptoms and the determined at least one aggregate score.

16. The computer program product of claim 15, wherein the plurality of burnout indicators are selected from a group comprising at least one of a plurality of written text, a plurality of emails, a plurality of calendar entries, and a plurality of wearable device data.

17. The computer program product of claim 15, wherein the program instructions to monitor and receive the plurality of burnout indicators further comprises:
- program instructions to use a plurality of detectors selected from a group comprising at least one of at least one workstation, at least one wearable device, at least one email server, and at least one cloud repository, to monitor and receive the plurality of burnout indicators.

18. The computer program product of claim 15, wherein the program instructions to monitor and receive the plurality of burnout indicators further comprises:
- program instructions to use IBM Watson™ Personality Insights and IBM Watson™ Tone Analyzer to analyze the plurality of burnout indicators.

19. The computer program product of claim 15, wherein the program instructions to detect the plurality of burnout events further comprises:
- program instructions to use a plurality of predictors to detect the plurality of burnout events based on the received plurality of predictor rules.

20. The computer program product of claim 15, wherein program instructions to present the at least one alert and the at least one recommendation further comprises:
- program instructions to use at least one of a messaging communication, a phone communication, and an email communication to present the at least one alert and the at least one recommendation.

* * * * *